United States Patent [19]

Smith, Jr. et al.

[11] Patent Number: 5,198,555
[45] Date of Patent: Mar. 30, 1993

[54] DIANHYDRIDES FROM CATALYZED REACTION OF MONOANHYDIDE MONOACID HALIDES WITH POLYALKYLATED MONONUCLEAR AROMATICS

[75] Inventors: Vincent F. Smith, Jr., Big Rock; Gary J. Gudac, Joliet, both of Ill.

[73] Assignee: Amoco Corporation, Chicago, Ill.

[21] Appl. No.: 794,992

[22] Filed: Nov. 15, 1991

[51] Int. Cl.$^5$ ............................................. C07D 307/80
[52] U.S. Cl. ........................................ 549/242; 549/241
[58] Field of Search ................................ 549/241, 242

[56] References Cited

U.S. PATENT DOCUMENTS

| | | | |
|---|---|---|---|
| 4,002,645 | 1/1977 | Sonnenberg | 549/242 |
| 4,329,292 | 5/1982 | Webb | 549/241 |
| 4,783,372 | 11/1988 | Pfeifer | 428/435 |
| 4,912,233 | 3/1990 | Kikuchi et al. | 549/241 |
| 4,937,317 | 6/1990 | Pratt et al. | 528/353 |
| 5,023,390 | 6/1991 | Abe et al. | 549/242 |
| 5,077,415 | 12/1991 | Jasne et al. | 549/242 |

FOREIGN PATENT DOCUMENTS

| | | | |
|---|---|---|---|
| 1565700 | 5/1969 | France | 549/242 |
| 1601094 | 9/1970 | France | 549/242 |
| 2-034376 | 5/1990 | Japan | 549/242 |

OTHER PUBLICATIONS

Eliel, Stereochemistry of Carbon Compounds, 1962, p. 173.

Primary Examiner—Cecilia Tsang
Attorney, Agent, or Firm—Rae K. Stuhlmacher; Wallace L. Oliver; Frank J. Sroka

[57] ABSTRACT

The invention relates to the preparation of novel dianhydrides of the formula:

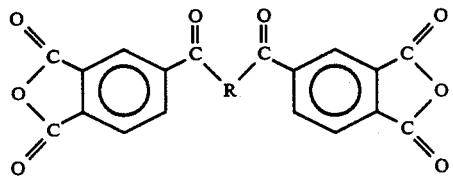

wherein R is a polyalkylated mononuclear aromatic radical, preferably a phenylene radical. The mononuclear aromatic radical may be substituted with from three to four lower alkyl radicals, preferably $C_1$–$C_4$ alkyl radicals. The dianhydrides are preferably made by the reaction of a monoanhydride monoacid halide and a polyalkylated mononuclear aromatic in the presence of a Friedel-Crafts catalyst under Friedel-Crafts reaction conditions. These dianhydrides ae useful reactants in the preparation of polyimides and epoxy curing agents.

9 Claims, No Drawings

DIANHYDRIDES FROM CATALYZED REACTION OF MONOANHYDIDE MONOACID HALIDES WITH POLYALKYLATED MONONUCLEAR AROMATICS

FIELD OF THE INVENTION

This invention relates to dianhydrides, particularly dianhydrides which are useful in the preparation of polyimides and epoxy curing agents.

BACKGROUND OF THE INVENTION

Polyimides are well-known and useful in the preparation of electrical insulation, structural materials, molding powders, films, composites and adhesives. These materials have good strength and electrical properties and can be used at high temperatures. However, many polyimides have the disadvantage of requiring fabrication from precursors, usually polyamic acid, because the polyimide itself is difficult to mold.

A number of moldable polyimides are available, but these require expensive raw materials and difficult manufacturing methods, making them relatively expensive. In view of these disadvantages, many attempts have been made to make a polyimide structure more processable and tractable and less expensive. For example, introduction of a group in addition to an imide, such as an ester or an amide link, has been used to render polyimides more processable. One disadvantage, however, is that the ester or similar group introduces a weak point in resistance to hydrolysis and oxidation at high temperatures. Thus, there is a need for new routes of synthesis of high performance polyimides.

Dianhydrides are well-known polyimide precursors. However, the presence of ketone functionality in dianhydride monomers is problematic for polyimide manufacture because crosslinking occurs through imine formation with diamines. Since such crosslinked polymers suffer from reduced processability, these reactions are undesirable for many applications.

In U.S. Pat. No. 4,002,645, a use of the Friedel-Crafts reaction is described for making bis-anhydrides derived from the monoacid halide of trimellitic anhydride which are useful as reactants for polyimide manufacture. The disclosed compounds are of the formula:

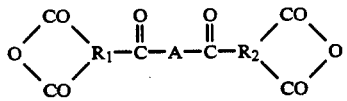

where $R_1$ and $R_2$ are trivalent aromatic radicals having vicinal carbon atoms (for example, 1,2-positions in benzene, 1,2- or 1,8- positions in naphthalene, etc.) from which stem the valence bonds to which the anhydride moieties are attached, and where A is a divalent polynuclear aromatic radical whose valence bonds stem from nuclear carbon atoms, preferably on separate nuclei. $R_1$ and $R_2$ can be selected from phenyl, naphthyl or biphenyl and A can be selected from diphenyl-Z, dinaphthyl-Z, dibenzofuran, fluorene, $C_1$ to $C_3$ alkylidene fluorene, carbazole and dibenzothiophene, wherein Z is O, S, $C_1$ to $C_3$ alkylidene or a single valence bond, and the point of attachment to the trivalent aromatic radicals of the carbonyl bridges between the trivalent and divalent aromatic radicals being other than ortho to the vicinal carbon atoms. Also disclosed in U.S. Pat. No. 4,002,645 is a process for manufacture of the above-described compounds which comprises treating a suitable derivative of an aromatic tricarboxylic acid, in which two carboxyl groups are bound to adjacent carbon atoms, preferably the monoanhydride monoacid chloride, with a polynuclear aromatic compound under Friedel-Crafts reaction conditions.

In U.S. Pat. No. 4,002,645, the use of a polynuclear aromatic such as biphenyl or diphenyl ether enables two or more adjacent rings to react with the monoanhydride monoacid chloride essentially independently. In the present invention, we have successfully prepared dianhydrides from mononuclear aromatics by what is believed to be the utilization of the strong activating influence of multiple alkyl groups distributed around the central ring. These groups not only enable preparation of novel dianhydrides, but also impart beneficial properties to polymers derived from these materials.

An example of a known polyimide material is LARC-TPI, which is derived from 3,3',4,4'-benzophenonetetracarboxylic dianhydride (BTDA) and 3,3'-diaminobenzophenone (3,3'-DABP) and is prepared in 2-methoxyethyl ether (diglyme).

In U.S. Pat. No. 4,937,317, there is disclosed a method of producing high molecular weight 4,4'-isophthaloyldiphthalic anhydride-methyl ethyl (IDPA-m-PDA) polyimides (LARC-I-TPI) that have the stated advantage over LARC-TPI of controlled molecular weight through end-capping. The dianhydrides for preparation of LARC-I-TPI are described in French Patent No. 1,601,094, Chem. Abstract, 76, 153352K (1972). In U.S. Pat. No. 4,783,372 other polyimides are described which also have been made using the dianhydrides described in French Patent No. 1,601,094. The dianhydrides of the present invention are distinguished over the above-referenced materials on the basis of the chemistry of their preparation and the end reaction products. Isophthaloyldiphthalic anhydride (IDPA) requires the specific reaction of IPA dichloride with orthoxylene, then oxidation. The dianhydrides of the present invention are prepared by attachment of the anhydride portion intact to the inner, central polyalkylated mononuclear aromatic.

Generally, in the acylation reactions of mononuclear aromatics, introduction of a first acyl group sufficiently deactivates the aromatic ring so that the introduction of a second acyl group is made very difficult. However, according to the present invention, it has been unexpectedly found that the presence and position of at least three alkyl groups of a mononuclear aromatic compound allow for the facile introduction of the second acyl group. Since in this special case such acyl group contains an anhydride moiety, unique dianhydrides are produced.

Our invention offers advantages of cost-efficiency, applicability to different dianhydrides and a different molecular geometry over IDPA. While not wishing to be bound by any theory, we believe that in the case of IDPA, all three aromatic rings are expected to be coplanar, whereas, in the polyalkylated central ring system of the dianhydrides of our invention, the inner ring is most likely twisted nearly 90° out of plane to relieve steric strain associated with otherwise coplanar alkyl groups, which is believed to impart enhanced solubility and processability to polyimides which may be derived from the dianhydrides of the invention. The molecular structure of the dianhydrides of the current invention minimizes undesirable crosslinking reactions by steric hindrance from the alkyl groups attached to the central aromatic.

SUMMARY OF THE INVENTION

We have prepared novel compounds of the formula:

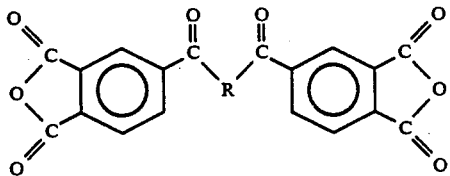

wherein R is a polyalkylated mononuclear aromatic radical, preferably a polyalkylated phenylene radical. The mononuclear aromatic radical may be substituted with from three to four lower alkyl groups, preferably $C_1$-$C_4$ alkyl groups, and most preferably methyl groups. Most preferably, R is a polyalkylated mononuclear aromatic selected from the group consisting of mesityl, duryl, isoduryl and pseudocumyl radicals. The dianhydrides are preferably made by the reaction of a monoanhydride monoacid halide with a polyalkylated mononuclear aromatic compound in the presence of a Friedel-Crafts catalyst under Friedel-Crafts reaction conditions. The dianhydrides are particularly useful as polyimide precursors, and may also be mixed with epoxy resins and used as curing agents.

BRIEF DESCRIPTION OF THE INVENTION

According to our invention, a polyalkylated mononuclear aromatic compound and a monoanhydride monoacid halide are reacted in the presence of a Friedel-Crafts catalyst. The mononuclear polyalkylated aromatic compound is preferably selected from the group consisting of mesitylene, durene, isodurene and pseudocumene. Most preferably the polyalkylated mononuclear aromatic compound is mesitylene.

The monoanhydride monoacid halide is preferably selected from the group consisting of 4-chloroformylphthalic anhydride (trimellitic anhydride acid chloride or TMAC), 3-chloroformylphthalic anhydride, the monoacid chloride of the 1,8-anhydride of 1,2,8- or 1,3,8- or 1,4,8-naphthalenetricarboxylic acid, the monoacid bromides of any of the above compounds, and mixtures thereof. Most preferably, the monoanhydride monoacid halide is trimellitic anhydride acid chloride.

The Friedel-Crafts catalysts useful in the invention are well-known to those skilled in the art and are described in U.S. Pat. No. 4,002,645, which is incorporated by reference herein. Preferably, the catalyst is boron trifluoride ($BF_3$) or a metal halide selected from the group consisting of aluminum chloride, zinc chloride and ferric chloride, and is most preferably a ferric chloride catalyst.

In a preferred process for manufacturing the dianhydrides of the invention, the polyalkylated mononuclear aromatic compound is added to the monoanhydride monoacid halide. The molar ratio of monoacid halide to aromatic is preferably greater than about 1.5:1 and most preferably about 2–3:1. Those skilled in the art will recognize that the lower the molar ratio of monoanhydride monoacid halide to aromatic, the less dianhydride product will be formed. When the molar ratio is about 2–3:1, optimal yields of dianhydride are obtained. This mixture must be protected from atmospheric moisture, for example, by use of a drying tube, or by use of a continuous blanket of dry nitrogen gas. With stirring and heating the mixture is brought to the melt/solution stage prior to the addition of any catalyst; during this stage of the process, no hydrogen halide evolution such as HCl is observed. A Friedel-Crafts catalyst is added to the mixture which preferably has been brought to a temperature sufficient to effect a reaction, typically, about 65°–75° C., preferably 70° C. While any Friedel-Crafts catalyst may be utilized and other ratios of catalyst to reactant may be employed in this process, preferably the catalyst is added in an amount which corresponds to about 1 millimole (mmole) per mole of monoanhydride monoacid halide. An immediate reaction takes place, and testing with moistened litmus at the top of the condenser outlet confirms large amounts of hydrogen halide being produced at this point of the process. Preferably, the reaction mixture is further heated to complete the reaction. Usually, the mixture is heated slowly up to the range of about 90°–130° C., preferably 100°–120° C., and held for a period of about 2 to 5 hours and, preferably, for about 3 hours. At the end of this time period, optionally, the mixture may be treated with a second portion of catalyst, preferably about 5 mmole of catalyst per mole monoacid halide and heated at a higher temperature of about 150°–250° C., preferably at about 210°–220° C. for about 2–5 hrs, preferably for about 3 hrs. During this time, the reaction mixture may pass through a semi-solid stage, which gradually returns to the liquid phase with continued heating. At the end of this second heating period, the mixture is poured out and allowed to cool for isolation of the dianhydride. Those skilled in the art will recognize that if the optional second portion of catalyst is not added, more catalyst will be used in the first addition.

Isolation of the dianhydride is made most convenient by the fact that when the hardened solid obtained directly from the reactor is first powdered and then stirred into a suitable organic solvent, preferably a low boiling aliphatic ketone, most preferably methyl ethyl ketone MEK (2-butanone), a brown powdery solid precipitates from the mixture. Filtration of this solid followed by oven-drying at about 125° C. produces the novel dianhydrides of the invention.

The dianhydrides are useful as unique monomers for the preparation of a variety of polyimides. In addition, the dianhydrides of the invention may be blended with epoxy resins and used as curing agents.

The invention described herein is illustrated, but not limited, by the following examples.

EXAMPLES

Example 1

Preparation of 2,4-Bis(4'-Trimellitoyl) Mesitylene Dianhydride

To a 500 ml resin kettle whose lid was equipped with a mechanical stirrer, a chilled water condenser, digital thermometer, and stoppered solids port, was charged 247 g (1.17 moles) solid trimellitic anhydride acid chloride (TMAC) and 64 g (0.53 mole) liquid mesitylene. Under a blanket of nitrogen and with the aid of a heating mantle, this mixture was stirred and heated to the point where a homogeneous bright yellow solution was obtained (65°–70° C.). Then 0.16 g (1 mmole) of anhydrous ferric chloride was added resulting in an immediate color change to deep red/brown and the generation of copious amounts of gaseous HCl, as evidenced by surface bubbling and the reaction of moistened blue litmus held at the top of the condenser. The temperature of the mixture was increased to 112° C. over 30 min and then held at 105°-120° C. over the next 2½ hrs; throughout that time, the evolution of gaseous HCl was continual. An additional 0.73 g (4.5 mmoles) of ferric chloride was added to the reaction mixture and the temperature was increased to 210°-220° C. and held at that point for an additional 3 hrs. By the end of that time period, HCl evolution slowed significantly. Stirring and heating were discontinued, and the molten product was poured from the reaction kettle into a foil trough for cooling and solidification. After the product had become a dark resinous solid, it was transferred from the foil to a mortar/pestle and crushed to a fine gray powder. When added to 650 ml of MEK (2-butanone), this gray powder first went into solution, but then quickly produced a brown/tan solid which was then filtered, air-dried, and oven-dried at 120° C. for 1½ hrs. The resulting product weighed 229 g (92% theoretical) and had a melting range of 173°-177° C. Acid number titrations gave 472 and 239 from pyridine-water and pyridine-methanol, respectively (theoretical values are 480 and 240). Infrared analysis of this material (as a solution in THF) shows the expected absorption bands for dianhydride (1780 and 1860 cm$^{-1}$) and for ketone (1680 cm$^{-1}$). Not unexpectedly, some smaller amounts of monoanhydride are formed in the reaction and the IR spectrum of the monoanhydride and the dianhydride are quite similar; the only distinctions appear to be the presence of a sharp band at 1610 cm$^{-1}$ in the spectrum of the monoanhydride and the presence of a sharp band at 1200 cm$^{-1}$ in the spectrum of the dianhydride.

EXAMPLE 2

Preparation of Monoanhydride Monoacid Halide-Diacylated Products of Polyalkyl Aromatics To a glass reactor fitted with stirrer, reflux condenser, and solid addition port was added the appropriate polyalkylated mononuclear aromatic listed in Table 1 with solid TMAC in a 1:2.1 molar ratio. After being blanketed with dry nitrogen, the reaction mixture was heated to the melt stage (~70° C.) and stirred. Anhydrous ferric chloride was added in an amount corresponding to 0.16 g per mole of TMAC, and the temperature was raised to 125° C. After being held at this temperature for 3 hrs, the mixture was treated with an additional 0.8 g ferric chloride per mole TMAC and further heated to 210° C., or reflux, whichever came first. After being held at this higher temperature for an additional 3 hrs, the mixture was removed from the reactor and allowed to cool.

The solidified samples were pulverized, suspended in MEK, and filtered. After drying in an oven, the solid was recrystallized from acetic acid:acetic anhydride mixtures (1:3 by weight).

All samples were then characterized by infrared spectroscopy, melting point, and acid number (A.N.) titrations of pyridine-water and pyridine-methanol solutions. Results are shown in Table 1.

TABLE 1

Characterization of Monoanhydride Monoacid Halide-Diacylated Products of Polyalkylated Aromatics

| Aromatic | Yield % | A. N. (Water) | | A. N. (MeOH) | | Melting Range °C.* |
|---|---|---|---|---|---|---|
| | | TAN | Obsd. | TAN | Obsd. | |
| Durene | 63 | 466 | 471 | 233 | 254 | 360–362** |
| Isodurene | 61 | 466 | 426 | 233 | 240 | 272–275 |
| Mesitylene | 92 | 478 | 486 | 239 | 251 | 188–189 |

TAN-Theoretical Acid Number
Obsd.-Observed Acid Number
*After one recrystallization from acetic acid-acetic anhydride
**Recrystallized from nitrobenzene The dianhydrides of the invention have several advantages. First, in using the dianhydrides for polyimide precursor materials, particularly with diamines such as aromatic diamines, for example, meta-phenylenediamine, the dianhydrides of the invention contain sterically shielded ketone functionality which minimizes crosslinking reactions involving the formation of ketimines. Second, the dianhydrides can be manufactured by a simple, cost-efficient method. Third, due to the unique presence of the polyalkyl aromatic moiety, the polyimides which may be derived from the dianhydrides have unique and improved properties such as enhanced solubility and processability.

From the above description, it is apparent that, while only certain embodiments of the invention have been set forth, alternative embodiments and various modifications will be apparent to those skilled in the art. These alternatives are considered equivalents and are within the spirit and scope of the present invention.

That which is claimed is:

1. A compound of the formula:

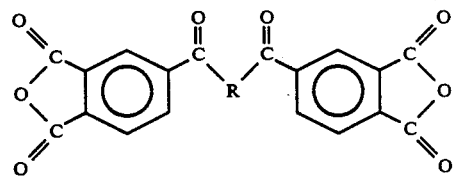

wherein R is a polyalkylated mononuclear aromatic radical selected from the group consisting of mesitylene, durene, isodurene and pseudocumene.

2. A composition made by the reaction of a polyalkylated mononuclear aromatic compound selected from the group consisting of mesitylene, durene, isodurene and pseudocumene and a monoanhydride monoacid halide in the presence of a Friedel-Crafts catalyst.

3. The composition of claim 2, wherein the monoanhydride monoacid halide is selected from the group consisting of 4-chloroformylphthalic anhydride, 3-chloroformylphthalic anhydride, the monoacid chloride of the 1,8-anhydride of 1,2,8- or 1,3,8- or 1,4,8-naphthalene tricarboxylic acid, the monoacid bromides of any of the above compounds, and mixtures thereof.

4. The composition of claim 2, wherein the Friedel-Crafts catalyst is selected from the group consisting of boron trifluoride, aluminum chloride, zinc chloride and ferric chloride.

5. The composition of claim 2, wherein the polyalkylated mononuclear aromatic is mesitylene, the monoanhydride monoacid chloride is trimellitic anhydride acid chloride and the Friedel-Crafts catalyst is ferric chloride.

6. The composition of claim 5, wherein the molar ratio of monoanhydride monoacid chloride to polyalkylated mononuclear aromatic is greater than about 1.5:1.

7. The composition of claim 6, wherein the molar ratio of monoanhydride monoacid chloride to polyalkylated mononuclear aromatic is about 2-3:1.

8. A process for making a compound of the formula:

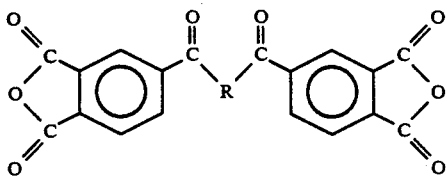

wherein R is a polyalkylated mononuclear aromatic radical selected from the group consisting of mesitylene, durene, isodurene and pseudocumene; said process comprising:

(a) mixing a polyalkylated mononuclear aromatic compound selected from the group consisting of mesitylene, durene, isodurene and pseudocumene with a monoanhydride monoacid halide;

(b) adding a Friedel-Crafts catalyst to the reaction mixture; and (c) isolating the compound by precipitation in an organic solvent.

9. A process for making a compound of the formula:

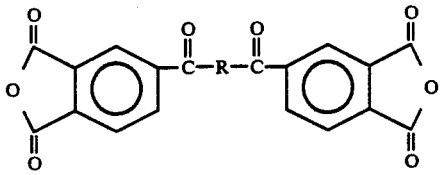

wherein R is a polyalkylated mononuclear aromatic radical selected from the group consisting of mesitylene, durene, isodurene and pseudocumene; said process comprising:

(a) mixing a polyalkylated mononuclear aromatic compound selected from the group consisting of mesitylene, durene, isodurene and pseudocumene with a monoanhydride monoacid halide;

(b) adding a Friedel-Crafts catalyst to the reaction mixture; and (c) isolating the compound by precipitation in methyl ethyl ketone.

* * * * *